(12) United States Patent
Elowe et al.

(10) Patent No.: US 9,464,017 B2
(45) Date of Patent: Oct. 11, 2016

(54) PROCESS FOR PREPARING DIARYL OXIDES BY DECARBOXYLATION

(71) Applicants: Dow Global Technologies LLC, Midland, MI (US); Rohm and Haas Company, Philadelphia, PA (US)

(72) Inventors: Paul R. Elowe, Midland, MI (US); Scott Han, Lawrenceville, NJ (US); Stephen W. King, League City, TX (US); Cynthia L. Rand, Sanford, MI (US)

(73) Assignees: DOW GLOBAL TECHNOLOGIES LLC; ROHM AND HAAS COMPANY

( * ) Notice: Subject to any disclaimer, the term of this patent is extended or adjusted under 35 U.S.C. 154(b) by 0 days.

(21) Appl. No.: 14/764,598

(22) PCT Filed: Mar. 19, 2014

(86) PCT No.: PCT/US2014/031153
§ 371 (c)(1),
(2) Date: Jul. 30, 2015

(87) PCT Pub. No.: WO2014/160562
PCT Pub. Date: Oct. 2, 2014

(65) Prior Publication Data
US 2016/0002134 A1    Jan. 7, 2016

Related U.S. Application Data

(60) Provisional application No. 61/805,663, filed on Mar. 27, 2013.

(51) Int. Cl.
*C07C 41/01* (2006.01)
*C09K 5/10* (2006.01)

(52) U.S. Cl.
CPC *C07C 41/01* (2013.01); *C09K 5/10* (2013.01)

(58) Field of Classification Search
None
See application file for complete search history.

(56) References Cited

U.S. PATENT DOCUMENTS

| | | | |
|---|---|---|---|
| 2,319,197 A | 5/1943 | Bachman et al. | |
| 4,596,680 A | 6/1986 | Jost et al. | |
| 5,075,022 A * | 12/1991 | Gambell | C09K 5/10 126/679 |
| 5,164,497 A | 11/1992 | King et al. | |
| 5,210,322 A | 5/1993 | King et al. | |
| 5,288,922 A | 2/1994 | Buske et al. | |
| 5,925,798 A | 7/1999 | Gambell et al. | |

FOREIGN PATENT DOCUMENTS

DE    1768374    11/1971

OTHER PUBLICATIONS

Witt et al., in Angew. Chem. Int. Ed., 1970, 9, 67.

* cited by examiner

*Primary Examiner* — Rosalynd Keys

(57) ABSTRACT

Provided is a process for the preparation of diaryl oxide compounds. The process uses a mixed metal oxide catalyst containing oxides of aluminum and magnesium to decarboxylate a diaryl carbonate compound to yield the diaryl oxide compound.

5 Claims, No Drawings

PROCESS FOR PREPARING DIARYL OXIDES BY DECARBOXYLATION

FIELD

This invention relates generally to a process for the preparation of diaryl oxide compounds. More particularly, the invention uses a mixed metal oxide catalyst containing oxides of aluminum and magnesium to decarboxylate a diaryl carbonate compound to yield the diaryl oxide compound.

BACKGROUND

Diaryl oxides (also referred to as diaryl ethers) are an important class of industrial materials. Diphenyl oxide (DPO), for instance, has many uses, most notably as the major component of the eutectic mixture of DPO and biphenyl, which is the standard heat transfer fluid for the concentrating solar power (CSP) industry. With the current boom in CSP has come a tightening of the supply of DPO globally and questions surrounding the sustainability of the technology have arisen.

Diaryl oxides are currently manufactured commercially via two major routes: reaction of a haloaryl compound with an aryl alcohol; or gas-phase dehydration of an aryl alcohol. The first route, for example where chlorobenzene reacts with phenol in the presence of caustic and a copper catalyst, typically leads to less pure product and requires high pressure (5000 psig), uses an expensive alloy reactor and produces stoichiometric quantities of sodium chloride.

The second route, which is a more desirable approach, accounts for the largest volume of diaryl oxides produced but requires a very active and selective catalytic material. For instance, DPO can be manufactured by the gas-phase dehydration of phenol over a thorium oxide (thoria) catalyst (e.g., U.S. Pat. No. 5,925,798). A major drawback of thoria however is its radioactive nature, which makes handling difficult and potentially costly. Furthermore, the supply of thoria globally has been largely unavailable in recent years putting at risk existing DPO manufacturers utilizing this technology. Additionally, other catalysts for the gas-phase dehydration of phenol, such as zeolite catalysts, titanium oxide, zirconium oxide and tungsten oxide, generally suffer from lower activity, significantly higher impurity content and fast catalyst deactivation.

In addition to the above routes, the synthesis of ether compounds through a mixed metal oxide catalyzed decarboxylation reaction has also been described, for instance in U.S. Pat. Nos. 5,164,497 and 5,210,322 (which references are incorporated herein by reference). These references disclose the decarboxylation of various organic carbonate compounds to form the corresponding ethers. The working examples in both references are focused on decarboxylation of non-aryl carbonate compounds. No aryl carbonate compounds are specifically illustrated in the examples and the ability of the process to decarboxylate the more hydrolytically unstable aryl carbonate compounds in favorable selectivity or yields was not recognized.

The lack of any specific examples in the above references regarding decarboxylation of diaryl carbonates is additionally not surprising since it is known from other literature that such a process is difficult to achieve. For instance, Witt et al., in Angew. Chem. Int. Ed., 1970, 9, 67, teaches that in order for the decarboxylation of diaryl carbonates to proceed, the carbonate compound must contain at least one ortho and/or para electron-withdrawing substituent. Furthermore, the reference teaches that useful yields are obtainable only from symmetrically substituted compounds (i.e., at least two electron withdrawing substituents), particularly p,p'-disubstituted, diphenyl carbonates.

Witt's teachings, that the diaryl carbonate must be substituted, are consistent with the teachings of U.S. Pat. No. 2,319,197. This reference describes a process whereby diphenylcarbonate (therefore no substitution) generates phenyl o-phenoxybenzoate (i.e. not diphenyloxide) when heated in the presence of a potassium carbonate catalyst.

With a chronic shortage of diaryl oxides such as DPO in sight, the pressing need to increase capacity, and the lack of commercially viable options, it has become crucial to develop new methods to produce diaryl oxides in a cost-effective and sustainable manner.

The problem addressed by this invention, therefore, is the provision of new processes for the manufacture of diaryl oxides.

STATEMENT OF INVENTION

We have now found that diaryl carbonates can be readily decarboxylated to the corresponding diaryl oxides under certain process conditions as described herein, including through the use of mixed metal oxide catalysts that contain oxides of aluminum and magnesium, through calcination of such catalysts, and through the exclusion of water from the reaction. Advantageously, it has been discovered that the process of the invention is suitable even for the decarboxylation of unsubstituted diaryl carbonates (to the corresponding unsubstituted diaryl oxides). This discovery is contrary to the teachings of the prior art discussed above.

In one aspect, therefore, there is provided a process for preparing a diaryl oxide compound, the process comprising: contacting a diaryl carbonate compound with a mixed metal oxide catalyst under decarboxylation conditions effective to produce the diaryl oxide compound, wherein the mixed metal oxide catalyst contains oxides of aluminum and magnesium and is calcined at a temperature of from 400 to 650° C. prior to the contacting step, and wherein water is substantially absent from the contacting step.

In another aspect, there is provided a process for producing a heat transfer fluid, the process comprising: (a) preparing a diaryl oxide compound by contacting a diaryl carbonate compound with a mixed metal oxide catalyst under decarboxylation conditions effective to produce the diaryl oxide compound, wherein the mixed metal oxide catalyst contains oxides of aluminum and magnesium and is calcined at a temperature of from 400 to 650° C. prior to the contacting step, and wherein water is substantially absent from the contacting step; (b) isolating the diaryl oxide from the mixed metal oxide catalyst and by-products; and (c) mixing the isolated diaryl oxide compound with biphenyl in an amount such that a eutectic mixture is formed.

DETAILED DESCRIPTION

Unless otherwise indicated, numeric ranges, for instance as in "from 2 to 10," are inclusive of the numbers defining the range (e.g., 2 and 10).

Unless otherwise indicated, ratios, percentages, parts, and the like are by weight.

As noted above, the invention provides processes for making diaryl oxide compounds via decarboxylation of diaryl carbonate compounds. The decarboxylation method is conducted in the presence of a mixed metal oxide catalyst that contains oxides of aluminum and magnesium. In addition, according to the method, the catalyst is calcined and the reaction is conducted in the substantial absence of water.

Diaryl carbonate compounds that may be employed in the process of the invention are generally of the formula Ar—O—(C=O)—O—Ar, where Ar independently represents an aryl group, such as phenyl. In preferred embodiments of the invention, Ar at both positions is unsubstituted phenyl (i.e., the compound is diphenyl carbonate).

The diaryl carbonate may optionally be dispersed or dissolved in a solvent for use in the method of the invention. Suitable solvents include hydroxyl-free solvents capable of solubilizing the diaryl carbonate such as, without limitation, toluene, benzene, and xylenes. Use of a solvent is preferred where the diaryl carbonate compound is a solid at room temperature.

As described above, the decarboxylation reaction is conducted in the presence of a catalyst. The catalyst is a mixed metal oxide material that contains oxides of aluminum and magnesium. Examples of suitable materials include hydrotalcites. Hydrotalcites are naturally occurring materials that are commercially available or that can be prepared by a person of ordinary skill in the art using established literature methods. The amount of decarboxylation catalyst used in the invention is not critical and can include, for instance, about 0.01 weight percent or less to about 10 weight percent or greater of the total weight of the starting diaryl carbonate compound.

The mixed metal oxide catalyst may optionally contain a binder and/or matrix material. Non-limiting examples of binders that are useful alone or in combination include various types of hydrated alumina, silicas and/or other inorganic oxide sols, and carbon. Upon heating, the inorganic oxide sol, preferably having a low viscosity, is converted into an inorganic oxide binder component. Non-limiting examples of matrix materials include clays or clay-type compositions.

The mixed metal oxide catalyst, including any binder or matrix materials, may be unsupported or supported. Non-limiting examples of suitable support materials include titania, alumina, zirconia, silica, carbons, zeolites, magnesium oxide, and mixtures thereof. Where the mixed metal oxide catalyst contains a binder, matrix or support material, the amount of active catalytic material in the mixture may be between 1 and 99 percent by weight based on the total weight of the catalyst (including the oxide, and any support, binder or matrix materials).

The mixed metal oxide catalyst may be formed into various shapes and sizes for ease of handling. For instance, the catalyst (including any binder, matrix, or support) may be in the form of pellets, spheres, or other shapes commonly used in the industry.

The mixed metal oxide catalyst used in the invention is calcined prior to the decarboxylation step. Calcination may be done at a temperature in the range of 400° C. to 650° C. for a period of time, such as about 20 min to 24 hours, preferably under an inert atmosphere, such as nitrogen.

In some embodiments, calcination is done at a temperature in the range of 550° C. to 650° C. It has been found that calcination at this temperature range results in a catalyst that is more selective for the desired diaryl oxide products at the expense of undesired by-products. In some embodiments, the diaryl oxide compound is selectively formed at a concentration of at least 8 weight percent based on the total weight of aryl products generated in the reaction (for instance, for diphenyl oxide synthesis, such aryl products may be, in addition to the diphenyl oxide, phenol and/or cresol).

The decarboxylation of the invention is conducted under conditions such that water is substantially absent. "Substantially absent" means a water content of 0.2 wt % or less, preferably 0.1 wt % or less, based on the total weight of the reactants (including catalyst and any solvent). In order to limit the presence of water in the reaction, methods known in the art can be employed. For instance, the solvent, such as toluene, may be dried prior to utilization. Drying methods include distillation, the use of molecular sieves, and other drying agents, such as sodium, calcium hydride, etc. If a dry solvent is used, further dilution of the diaryl carbonate feed will help in reducing the overall water content. Furthermore, the diaryl carbonate compound may itself be dried by methods known in the art, such as for instance recrystallization. In addition, the process may be carried out under an air-free environment to prevent intrusion of moisture from the air.

In a typical procedure for carrying out the method of the invention, the mixed metal oxide catalyst is charged to a reactor heated to calcination temperature under inert atmosphere. The reactor is then cooled and a feed of the diaryl carbonate, optionally in a solvent, is passed over the catalyst bed, for instance at atmospheric pressure. The weight hourly space velocity (WHSV) of the carbonate compound over the catalyst is not critical and may, for instance, be in the range of 0.01 $g \cdot g_{cat}^{-1} \cdot h^{-1}$ (grams of DPC per gram of catalyst per hour) to 20 $g \cdot g_{cat}^{-1} \cdot h^{-1}$. In some embodiments, a residence time of 0.05 $g \cdot g_{cat}^{-1} \cdot h^{-1}$ to 2 $g \cdot g_{cat}^{-1} \cdot h^{-1}$ may be preferred. The decarboxylation is preferably conducted at a temperature ranging from 100° C. to 700° C., preferably at 200° C. to 500° C., more preferably 350° C. to 400° C.

Following the reaction, the diaryl oxide product is recovered from the catalyst and optionally further purified. Unreacted diaryl carbonate and other reaction by-products may be separated using methods known in the art. Such methods include but are not limited to distillation, crystal refining, simulated moving bed technique or a combination thereof. Moreover, alcohol substituted aryl byproduct (e.g., phenol) may be isolated and converted back to a diaryl carbonate (e.g., diphenyl carbonate) using methods known to those skilled in the art. This diaryl carbonate may be used in the process of the invention, thus further increasing selectivity of the desired product and reducing the amount of unwanted byproducts.

The diaryl oxides prepared by the invention are useful in a variety of applications. For instance, they may be useful as high temperature solvents, as intermediates in preparing flame retardants and surfactants, as components in heat transfer fluids, as high performance lubricants, and/or as intermediates in preparing other compounds. In some embodiments, a preferred diaryl oxide prepared by the process of the invention is diphenyl oxide (DPO).

In some embodiments, a preferred use of the diaryl oxide, such as DPO, is in high temperature heat transfer fluids. High temperature heat transfer fluids may be prepared by making the diaryl oxide according to the process described above and then mixing the diaryl oxide with biphenyl. The amounts necessary to provide a suitable fluid can be readily determined by a person with ordinary skill in the art. For diphenyl oxide and biphenyl, the amount of DPO may be, for instance, from 70 to 75 weight percent based on the total weight of the DPO and biphenyl. A preferred amount of DPO is that required to form a eutectic mixture with the biphenyl, which is about 70 to 75, preferably about 73.5, weight percent based on the total weight of the DPO and biphenyl.

Some embodiments of the invention will now be described in detail in the following Examples.

EXAMPLES

Example 1

In all cases, the catalyst used is a commercially available hydrotalcite catalyst from Süd-Chemie and designated T-2577. The reactions are carried out in a standard 1" o.d. fixed bed reactor with a single zone electrical furnace. A typical experiment involves charging the reactor with 40 mL of catalyst and pretreating the catalyst in-situ at 450-650° C. with a $N_2$ flow of 360 mL/min for 1 hr. The reactor is then cooled to the desired reaction temperature and a feed containing 20 wt % diphenylcarbonate dissolved in toluene is passed over the catalyst bed at atmospheric pressure and a weight hourly space velocity of 0.1 $g \cdot g_{cat}^{-1} \cdot h^{-1}$ (grams of DPC per gram of catalyst per hour) with the same $N_2$ feed flow. Total residual feed water content is analyzed to be 0.07 wt %. Products are analyzed by gas chromatography.

Three different catalyst pretreatment temperatures are used: 450° C., 550° C., and 650° C. The data obtained are summarized in the following table.

| Catalyst | Pretreatment Temp. ° C. | Reaction Temp. ° C. | DPC conv., % | DPO sel., % | Phenol* sel., % | Cresol sel., % |
|---|---|---|---|---|---|---|
| T-2577 | 450 | 350 | 69.3 | 4.6 | 92.3 | 3.1 |
| | 450 | 375 | 75.4 | 4.3 | 94.3 | 2.1 |
| | 450 | 400 | 78.2 | 2.8 | 95.0 | 2.2 |
| | 550 | 350 | 57.8 | 8.4 | 91.6 | 0.0 |
| | 550 | 400 | 8.5 | 15.2 | 84.8 | 0.0 |
| | 650 | 350 | 36.4 | 15.8 | 82.5 | 1.7 |
| | 650 | 375 | 12.9 | 22.5 | 77.2 | 0.3 |
| | 650 | 400 | 7.4 | 10.0 | 89.5 | 0.5 |

*The phenol byproduct may be used to generate DPC starting material which may then be run through the process of the invention to generate more DPO.

The results in the table show that DPO selectivity is significantly improved when catalyst pretreatment temperature is increased. Increased DPO selectivities came at the expense of undesired phenol and cresol byproducts.

The invention claimed is:

1. A process for preparing an unsubstituted diaryl oxide compound, the process comprising:
    contacting a diaryl carbonate compound with a mixed metal oxide catalyst under decarboxylation conditions effective to produce the diaryl oxide compound,
    wherein the diaryl carbonate compound is diphenyl carbonate; and
    wherein the mixed metal oxide catalyst contains oxides of aluminum and magnesium and is calcined at a temperature of from 400 to 650° C. prior to the contacting step, and
    wherein the concentration of water is 0.2 weight-percent or less based on the total weight of the reactants, including catalyst and any solvent, in the contacting step.

2. The process of claim 1 wherein the mixed metal oxide catalyst is calcined at a temperature of from 550 to 650° C.

3. The process of claim 1 wherein the mixed metal oxide catalyst is calcined at a temperature of from 550 to 650° C., the elevated temperature for the contacting step is from 350 to 400° C., and wherein the diaryl oxide compound is selectively formed at a concentration of at least 8 weight percent based on the total weight of aryl products generated.

4. The process of claim 1 wherein the diaryl carbonate compound is present in a solvent.

5. A process for producing a heat transfer fluid, the process comprising:
    (a) preparing an unsubstituted diaryl oxide compound according to the process of claim 1 by contacting a diaryl carbonate compound with a mixed metal oxide catalyst under decarboxylation conditions effective to produce the diaryl oxide compound, wherein the mixed metal oxide catalyst contains oxides of aluminum and magnesium and is calcined at a temperature of from 400 to 650° C. prior to the contacting step, and wherein the concentration of water is 0.2 weight-percent of less based on total weight of the reactants, including catalyst and any solvent, during the contacting step
    (b) isolating the diaryl oxide from the mixed metal oxide catalyst; and
    (c) mixing the isolated diaryl oxide compound with biphenyl in an amount such that a eutectic mixture is formed.

* * * * *